(12) United States Patent
Lu

(10) Patent No.: US 7,663,740 B2
(45) Date of Patent: Feb. 16, 2010

(54) OPTICAL POWER MEASURING APPARATUS CAPABLE OF MONITORING STATUS OF OPTICAL FIBER CONTACT END

(75) Inventor: Tien-Hsiang Lu, Taipei (TW)

(73) Assignee: Inventec Multimedia & Telecom Corporation, Taipei (TW)

( * ) Notice: Subject to any disclaimer, the term of this patent is extended or adjusted under 35 U.S.C. 154(b) by 262 days.

(21) Appl. No.: 11/798,157

(22) Filed: May 10, 2007

(65) Prior Publication Data
US 2008/0278709 A1    Nov. 13, 2008

(51) Int. Cl.
*G01N 21/00* (2006.01)
(52) U.S. Cl. ........................................ 356/73.1; 356/72
(58) Field of Classification Search .................. 356/73.1
See application file for complete search history.

(56) References Cited

U.S. PATENT DOCUMENTS

| 5,119,383 | A | * | 6/1992 | Duling et al. ................. 372/18 |
|---|---|---|---|---|
| 6,034,718 | A | * | 3/2000 | Hattori .......................... 348/61 |
| 6,259,719 | B1 | * | 7/2001 | Cunningham et al. .......... 372/99 |
| 2003/0030787 | A1 | * | 2/2003 | Beller et al. ................ 356/73.1 |
| 2005/0259242 | A1 | * | 11/2005 | Bridge et al. ............... 356/73.1 |
| 2008/0246957 | A1 | * | 10/2008 | Beranek ..................... 356/73.1 |

* cited by examiner

*Primary Examiner*—Gregory J Toatley, Jr.
*Assistant Examiner*—Rebecca C Slomski
(74) *Attorney, Agent, or Firm*—Stout, Uxa, Buyan & Mullins, LLP

(57) ABSTRACT

The present invention provides an optical power measuring apparatus capable of monitoring the status, such as cleanness, of an optical fiber contact end face. The disclosed optical power measuring apparatus includes a microscope camera module, an illuminating module, an optical element, an optical power detection unit, a display unit and a central processing unit. The present invention may switch between optical fiber contact end status monitoring and optical power measurement. The apparatus can simplify the complicated steps for an optical fiber to insert to and pull from an optical microscope and then insert to an optical power meter. It can help a user to measure the correct optical power rapidly.

15 Claims, 2 Drawing Sheets

OPTICAL POWER MEASURING APPARATUS CAPABLE OF MONITORING STATUS OF OPTICAL FIBER CONTACT END

BACKGROUND OF THE INVENTION

1. Field of the Invention

The present invention generally relates to an optical power measuring apparatus, and more particularly to an optical power measuring apparatus capable of monitoring status of the optical fiber contact end face by using an optical element with specific optical reflection characteristic as well as a microscope camera module.

2. Description of the Prior Art

Traditional optical power meter can only detect the optical power passing through an optical fiber, while lacking the capability of examining the status of the fiber under measuring. However, the cleanness of the contact end face of the optical fiber under measuring would affect the transmission of an optical signal. A dirty contact end can lead to errors ranged from several dBs to several tens of dBs on measuring the optical power. Accordingly, before measuring the optical power, an optical microscope is usually employed to examine the optical fiber contact end face for identifying the cleanness thereof. The optical fiber will be inserted to and then pulled from an optical microscope for the cleanness identifying process. If the contact end is clean, then it will be inserted to the optical power meter; otherwise, the user should clean the contact end before inserting the optical fiber to the optical power meter. By this way, it is inconvenient to a user for measuring optical power due to the overhead of inserting and pulling.

In view of the inconvenience mentioned above, a need has arisen to propose an optical power measuring apparatus combined with the function of an optical microscope. When the optical fiber inserts to the apparatus of the present invention, a user can examine whether the contact end thereof is clean or dirtied. If the condition is normal, the user can easily measure the optical power can get an accurate power value. Such a convenient apparatus will help improve the development of optical communication technology.

SUMMARY OF THE INVENTION

In view of the foregoing, there is a need to decrease the steps of examining the cleanness of an optical fiber contact end face. One object of the present invention is to provide an optical power measuring apparatus possessing the function of an optical microscope. By using properties of optical reflection and transmission of an optical element to perform the functions of examining an optical fiber contact end face or measuring the optical power, it is more convenient to the user.

According to the object mentioned above, the present invention provides an optical power measuring apparatus capable of monitoring the status of the optical fiber contact end face. The apparatus includes a microscope camera module which is used to receive the visible light signal of an optical fiber contact end face image and transform the signal into a digital image signal; an optical power detection unit which is used to receive the optical power transmitted through the optical fiber and transform it into a specific electric signal; a display unit which is used to display image; and a central processing unit which is used to transform the digital image signal and the specific electric signal into a first display signal and a second display signal respectively as well as decide to pass the first display signal or the second display signal to the display unit such that a user may monitor the status of the optical fiber contact end face or the value of the optical power signal.

The optical power measuring apparatus capable of monitoring the status of the optical fiber contact end face of the present invention may further include an illuminating module which is used to emit visible light to help forming the image of the optical fiber contact end face; and an optical element which is used to reflect the visible light signal of the contact end face image to the microscope camera module. The optical reflection rate of the optical element may change according to the intensity of the visible light.

The optical power measuring apparatus capable of monitoring the status of the optical fiber contact end face of the present invention may further include a human interface unit which is used to receive a user's command to switch the target monitored on the display unit between image of the optical fiber contact end face or the optical power value.

DETAILED DESCRIPTION OF THE INVENTION

Figure 1A:
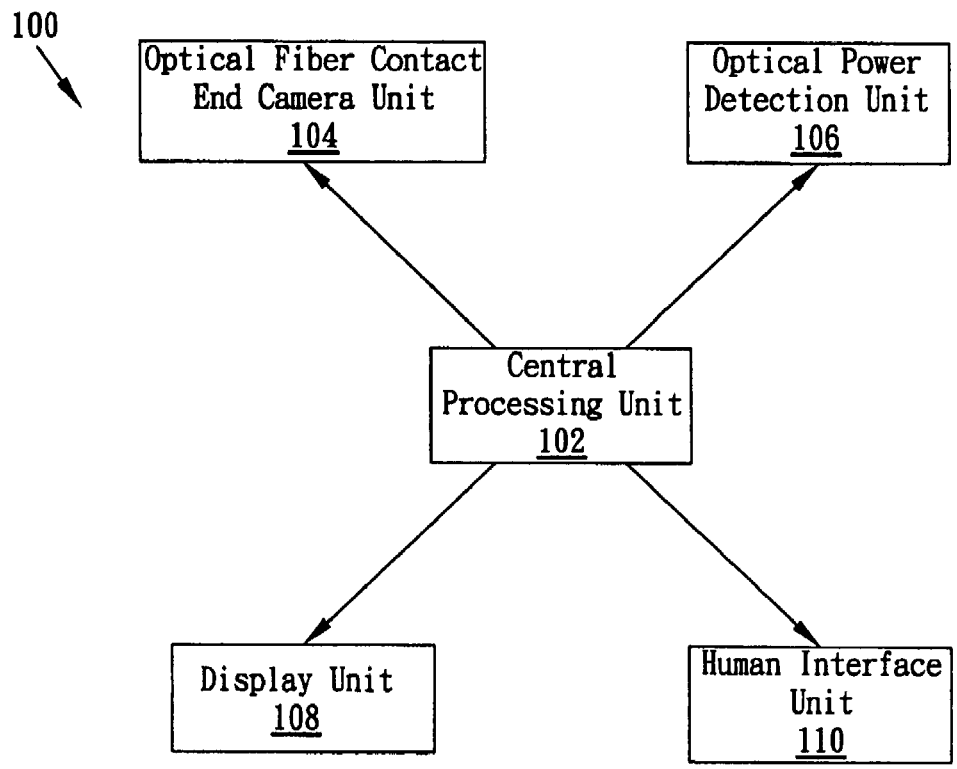
FIG. 1A shows a schematic block diagram of the optical power measuring apparatus capable of monitoring the status of the optical fiber contact end face according to a preferred embodiment of the present invention.

Following is the detailed description of the present invention. FIG. 1A shows a schematic block diagram of the optical power measuring apparatus 100 capable of monitoring the status of the optical fiber contact end face according to a preferred embodiment of the present invention, the optical power measuring apparatus 100 including a central processing unit 102, an optical fiber contact end camera unit 104, an optical power detection unit 106, a display unit 108 and a human interface unit 110. The present invention mainly uses the central processing unit 102 as a core control unit which connects to and controls the optical fiber contact end camera unit 104, the optical power detection unit 106, the display unit 108 and the human interface unit 110.

The central processing unit 102 may be a general microprocessor executing programs stored in memory and receiving a user's commands from the human interface unit 110 to perform necessary control operations of the optical fiber contact end camera unit 104, the optical power detection unit 106, and the display unit 108. These control operations include, but not limit to, initializing every unit mentioned above, zooming or panning the optical fiber contact end camera unit 104, changing optical power sensitivity settings of the optical power detection unit 106, and adjusting visual properties of the display unit 108 such as color or brightness. The memory mentioned above may be a built in the central processing unit 102, or it may also be a standalone external memory such as a dynamic random access memory (DRAM) or any kind of read only memory (ROM).

Figure 1B:
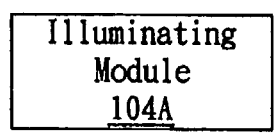
FIG. 1B shows a schematic block diagram of an optical fiber contact end camera unit according to one embodiment of the present invention.
Figure 1B:
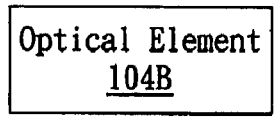
Figure 1B:
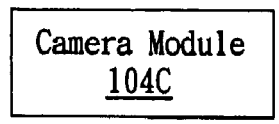

The optical fiber contact end camera unit 104 enables a user to examine whether the optical fiber contact end has faulty conditions or not and take photographs if necessary. Referring to FIG. 1B which shows a schematic block diagram of an optical fiber contact end camera unit 104 according to one embodiment of the present invention. As shown in FIG. 1B, the optical fiber contact end camera unit 104 includes an illuminating module 104A, an optical element 104B, and a microscope camera module 104C. The microscope camera module 104C may have the micrograph capability (i.e. capability to magnify the image), so as to present the image of the cleanness status of an optical fiber contact end face on the display unit 108. The camera module 104C is configured to receive the visible light signal of the image of the optical fiber contact end face and transform the visible light signal into a digital image signal. The digital image signal is processed by the central processing unit 102 and transformed to a first display signal which is then output to the display unit for a user to monitor. According to another embodiment of the present invention, the microscope camera module 104C also connects to the display unit 108. It may transform a digital image signal into the first display signal directly or under the control of the central processing unit 102, and then the central processing unit 102 is used to control if the first display signal is output to the display unit 108 or not. The camera module 104C may include a color or black-and-white image sensor, an optical lens module with micrograph capability as well as other control circuits. The image sensor can be a CCD (charge coupled device) element or a CMOS (complementary metal-oxide-semiconductor) element or other element capable of detecting images. As for functions and properties of the illuminating module 104A and the optical element 104B, please refer to the description of FIG. 2.

Come back to FIG. 1A. The function of the optical power detection unit 106 is to measure the optical power transmitted through the optical fiber. It may receive the optical power from the optical fiber contact end and transform the optical power into a specific electric signal. The central processing unit 102 may transform the specific electric signal into a second display signal which is then transmitted to the display unit 108 to be monitored by an end user. According to another embodiment of the present invention, the optical power detection unit 106 may include the circuit that transforms the specific electric signal into the second display signal and connect to the display unit 108. The optical power detection 106 may include optical power measurement elements, such as a photo diode, as well as other control circuits.

The display unit 108 is used for displaying the image of the optical fiber contact end face. It can be a liquid crystal display or any device which possesses a function of image display. The display unit 108 may be a color or monochrome type and there is no special limit about the size thereof. The display unit 108 may also include display elements, such as light emitting diodes, to show the system status of the optical power apparatus 100.

The human interface unit 108 provides an interface for a user to operate the optical power apparatus 100. It may include peripheral input devices such as the buttons, the keyboard, and/or the pointing devices (such as the trackball or the mouse). As mentioned above, the central processing unit 102 receives a user's command from the human interface unit 110 to perform necessary control operations of other units in the optical power apparatus 100. For example, it switches the display content of the display unit 108 between the image of the optical fiber contact end face and the value of the measured optical power.

Figure 2:
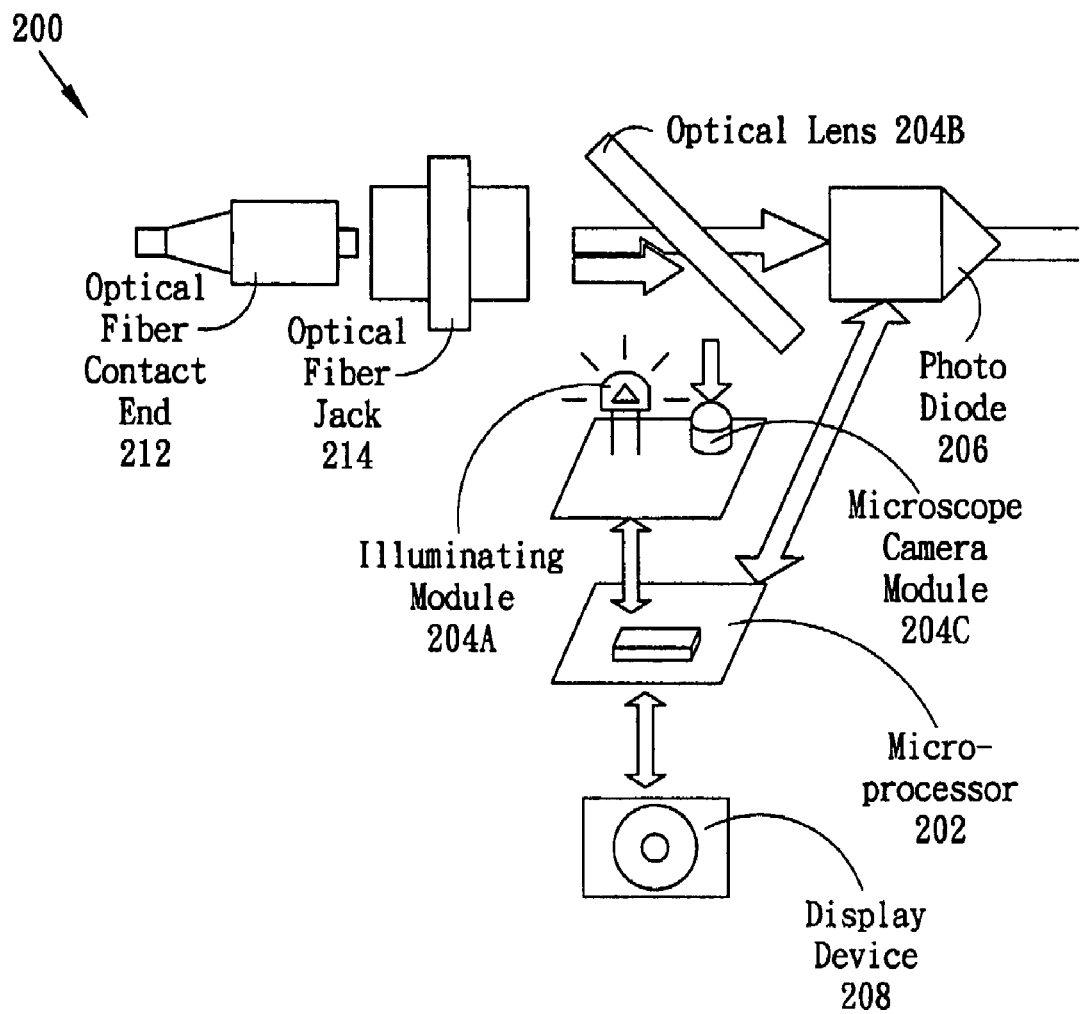
FIG. 2 shows a detailed diagram illustrating an optical power measuring apparatus capable of monitoring the status of the optical fiber contact end face according to a preferred embodiment of the present invention.

FIG. 2 shows a detailed diagram illustrating the optical power measuring apparatus 200 capable of monitoring the status of the optical fiber contact end face according to a preferred embodiment of the present invention, the optical power measuring apparatus 200 including an optical fiber jack 214, an optical lens 204B, a photo diode 206, an illuminating module 204A, a microscope camera module 204C, a microprocessor 202, and a display device 208. Similar to FIG. 1, the microprocessor 202 connects to and controls the photo diode 206, the illuminating module 204A, the microscope camera module 204C and the display device 208.

The optical fiber jack 214 is used for connecting the optical fiber contact end 212 under measuring. It has a function of mounting the contact end and works as a connector between the optical fiber contact end 212 and the optical power apparatus 200.

The optical lens 204B corresponds to the optical element 104B mentioned above. It may be a glass lens with a specific coating thereon such that the optical reflection rate thereof is enhanced under a stronger light and the optical transmission rate thereof dominates in the dark. The illuminating module 204A (corresponding to the illuminating module 104A mentioned above) may include a light emitting diode which can emits visible illuminating light to improve the image clearness of the optical fiber contact end face. The microscope camera module 204C, as mentioned above, is used to receive the visible light signal of the optical fiber contact end face image and transform the visible light signal into a digital image signal. The digital image signal may be output to the display device 208 after being transformed into a display signal, so as to facilitate examining whether the optical fiber contact end face is clear or not. As can be noted by arrangement of FIG. 2, when the illuminating module 204A is on, the optical lens 204B will have a better reflective rate such that the visible light signal representing the optical fiber contact end face image may be reflected to the microscope camera module 204C in higher fidelity.

The display device 208, as mentioned above, may be a general liquid crystal display to present the image of the optical fiber contact end face. The photo diode 206 configured to measure the optical power corresponding to the optical power detection unit 106 of FIG. 1.

One aspect of the present invention is to use the optical lens 204B which has reflection property changed in response to the intensity of visible illuminating light. A user can examine status of the optical fiber contact end face by invoking a better reflection rate of the optical lens 204B (by turning on the illuminating module 204A, for example); on the contrary, the optical power passing through the optical fiber may be measured by invoking a better transmission rate thereof. By controlling the light emitting diode of the illuminating module 204A, it can help a user to examine the optical fiber contact end status. When the light emitting diode is on, the optical lens 204B becomes a mirror to reflect the image of the optical fiber contact end face to the microscope camera module 204C such that the contact end may be examined clearly; when the light emitting diode is off, the optical element 204B becomes a lens to pass the optical signal from the optical fiber to the photo diode 206 such that the optical power may be measured. By doing so, a user can simplify the steps of measuring optical power. It only includes one action of inserting and pull, instead of many times of inserting and pull as necessary in prior art.

Although specific embodiments have been illustrated and described, it will be appreciated by those skilled in the art that various modifications may be made without departing from the scope of the present invention, which is intended to be limited solely by the appended claims.

What is claimed is:

1. An optical power measuring apparatus capable of monitoring status of an optical fiber contact end face, comprising:

a microscope camera module, configured to receive a visible light signal of an image of the optical fiber contact end face and transform the visible light signal into a digital image signal;

an optical power detection unit, configured to receive an optical power signal passing through the optical fiber and transform the optical power signal into a specific electric signal;

a display unit;

a central processing unit, configured to control the transformation of the digital image signal and the specific electric signal into a first display signal and a second display signal respectively and output the first display signal or the second display signal to the display unit such that a user can monitor the cleanness status of the optical fiber contact end face or a value of the optical power signal on the display unit;

an illuminating module, configured to emit a visible illuminating light to facilitate forming the image of the optical fiber contact end face; and an optical element, configured to reflect the visible light signal to the microscope camera module and having an optical reflection rate that changes in response to intensity of the visible illuminating light.

2. The apparatus of claim 1, wherein the illuminating module is a light emitting diode and when the intensity of the visible illuminating light becomes stronger, the optical reflection rate of the optical element becomes larger.

3. The apparatus of claim 2, wherein the optical element is a glass lens with a specific coating thereon.

4. The apparatus of claim 1, wherein the microscope camera module comprises an image sensor and an optical lens module.

5. The apparatus of claim 4, wherein the image sensor is a CCD (charge coupled device) type or a CMOS (complementary metal-oxide-semiconductor) type image sensor.

6. The apparatus of claim 1, wherein the optical power detection unit comprises a photo diode.

7. The apparatus of claim 1, wherein the display unit is a liquid crystal display.

8. An optical power measuring apparatus capable of monitoring status of an optical fiber contact end face, comprising:

a microscope camera module, configured to receive a visible light signal representing an image of the optical fiber contact end face and transform the visible light signal into a digital image signal;

an illuminating module, configured to emit a visible illuminating light to facilitate forming the image of the optical fiber contact end face;

an optical element, configured to reflect the visible light signal to the microscope camera module, optical reflection rate of the optical element being changed in response to intensity of the visible illuminating light;

an optical power detection unit, configured to receive an optical power signal passing through the optical fiber and transform the optical power signal into a specific electric signal;

a display unit;

a central processing unit, configured to control the transformation of the digital image signal and the specific electric signal into a first display signal and a second display signal respectively and output the first display signal or the second display signal to the display unit such that a user can monitor the cleanness status of the optical fiber contact end face or a value of the optical power signal on the display unit; and a human interface unit, configured to input a user's command for switching a target monitored on the display unit between the image of the optical fiber contact end face and the value of the optical power signal.

9. The apparatus of claim 8, wherein the illuminating module is a light emitting diode and when the intensity of the visible illuminating light becomes stronger, the optical reflection rate of the optical element becomes larger.

10. The apparatus of claim 9, wherein the optical element is a glass lens with a specific coating thereon.

11. The apparatus of claim 8, wherein the microscope camera module comprises an image sensor and an optical lens module.

12. The apparatus of claim 11, wherein the image sensor is a CCD (charge coupled device) type or a CMOS (complementary metal-oxide-semiconductor) type image sensor.

13. The apparatus of claim 8, wherein the optical power detection unit includes a photo diode.

14. The apparatus of claim 8, wherein the display unit is a liquid crystal display.

15. The apparatus of claim 8, wherein the human interface unit comprises a button.

* * * * *